US00PP29386P3

(12) United States Plant Patent
Suphachadiwong

(10) Patent No.: US PP29,386 P3
(45) Date of Patent: Jun. 12, 2018

(54) ***VANDA* PLANT NAMED SPCDW1521**

(50) Latin Name: ***Vanda* Jones ex R. Br.**
Varietal Denomination: SPCDW1521

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 45 days.

(21) Appl. No.: 15/530,041

(22) Filed: Nov. 23, 2016

(65) Prior Publication Data

US 2017/0156248 P1 Jun. 1, 2017

(30) Foreign Application Priority Data

Nov. 27, 2015 (QZ) ..... PBR 2015/2872

(51) Int. Cl.
*A01H 5/02* (2018.01)

(52) U.S. Cl.
USPC ..... Plt./311

(58) Field of Classification Search
None
See application file for complete search history.

*Primary Examiner* — Anne Marie Grunberg
(74) *Attorney, Agent, or Firm* — Samuel R. McCoy, Jr.

(57) ABSTRACT

A new and distinct cultivar of *Vanda* plant named 'SPCDW1521' which is characterized by long, dark green foliage and large flowers which are loosely held on a tall inflorescence, violet sepals and petals with prominent dark violet reticulate venation, sepals and petals which are slightly spiraled in a propeller-like fashion, a very dark violet labellum, and the stability of these characteristics from generation to generation.

3 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1521'.

CROSS REFERENCE TO RELATED APPLICATIONS

This application claims priority to the Community Plant Variety Rights application number 2015/2872, filed Nov. 27, 2015, which is herein incorporated by reference.

BACKGROUND OF THE INVENTION

Parentage: The *Vanda* variety 'SPCDW1521' is the result of a planned breeding program. The new variety originated as a seedling from the crossing of *Vanda* 'M217' (not patented), the seed parent, with *Vanda* 'CS76' (not patented), the pollen parent. Both parents were developed by, and are owned by, the inventor and were never commercially released. The crossing was made by the inventor in his research greenhouse in Bangphra, Thailand in October of 1995.

The new variety was first selected in November of 1999, in a research greenhouse in Bangphra, Thailand belonging to the inventor. After identifying the new variety as a potentially interesting selection, the inventor continued confidential testing and propagation of 'SPCDW1521', assessing stability of the unique characteristics of this variety.

Asexual Reproduction: Asexual reproduction of the new cultivar 'SPCDW1521', by way of mericloning, was first initiated in January of 2008 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1521' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1521'. These characteristics in combination distinguish 'SPCDW1521' as a new and distinct *Vanda* cultivar:

1. *Vanda* 'SPCDW1521' exhibits large flowers loosely held on a tall inflorescence; and
2. *Vanda* 'SPCDW1521' exhibits long, dark green foliage; and
3. *Vanda* 'SPCDW1521' exhibits violet sepals and petals with prominent dark violet reticulate venation; and
4. *Vanda* 'SPCDW1521' exhibits sepals and petals which are slightly spiraled in a propeller-like fashion; and
5. *Vanda* 'SPCDW1521' exhibits a very dark violet labellum.

BOTANICAL DESCRIPTION OF THE PLANT

Figure 1:
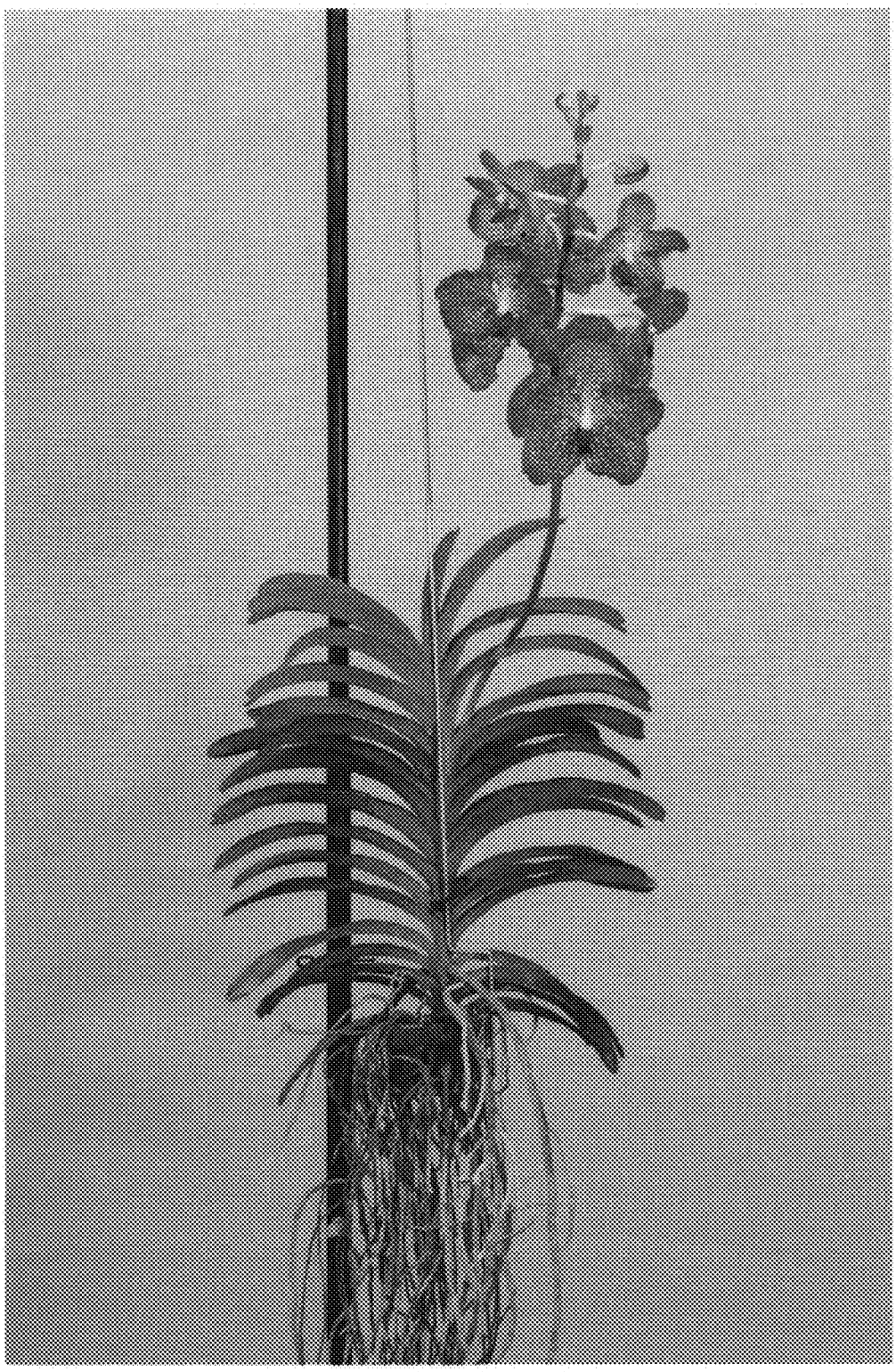
FIG. 1 illustrates, as nearly true as it is reasonably possible to make the same in color photographs of this type, an exemplary plant of 'SPCDW1521' grown in a commercial greenhouse in Honselersdijk, the Netherlands. This plant is approximately 6 years old from the time of mericloning, shown planted in an 8 by 8 cm container.
Figure 2:
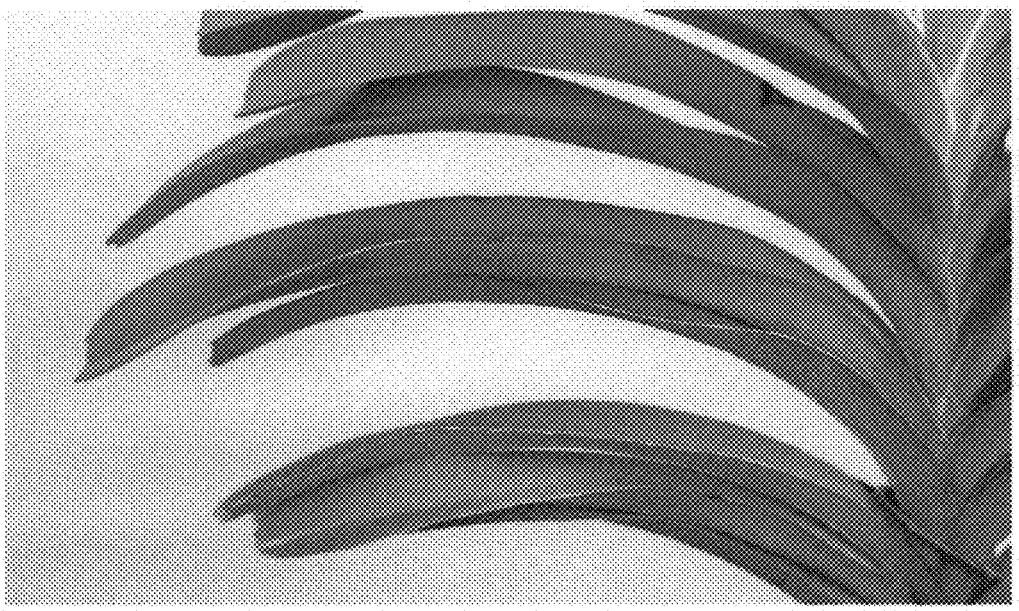
FIG. 2 illustrates, as nearly true as it is reasonably possible to make the same in color photographs of this type, the typical foliage of 'SPCDW1521'.
Figure 3:
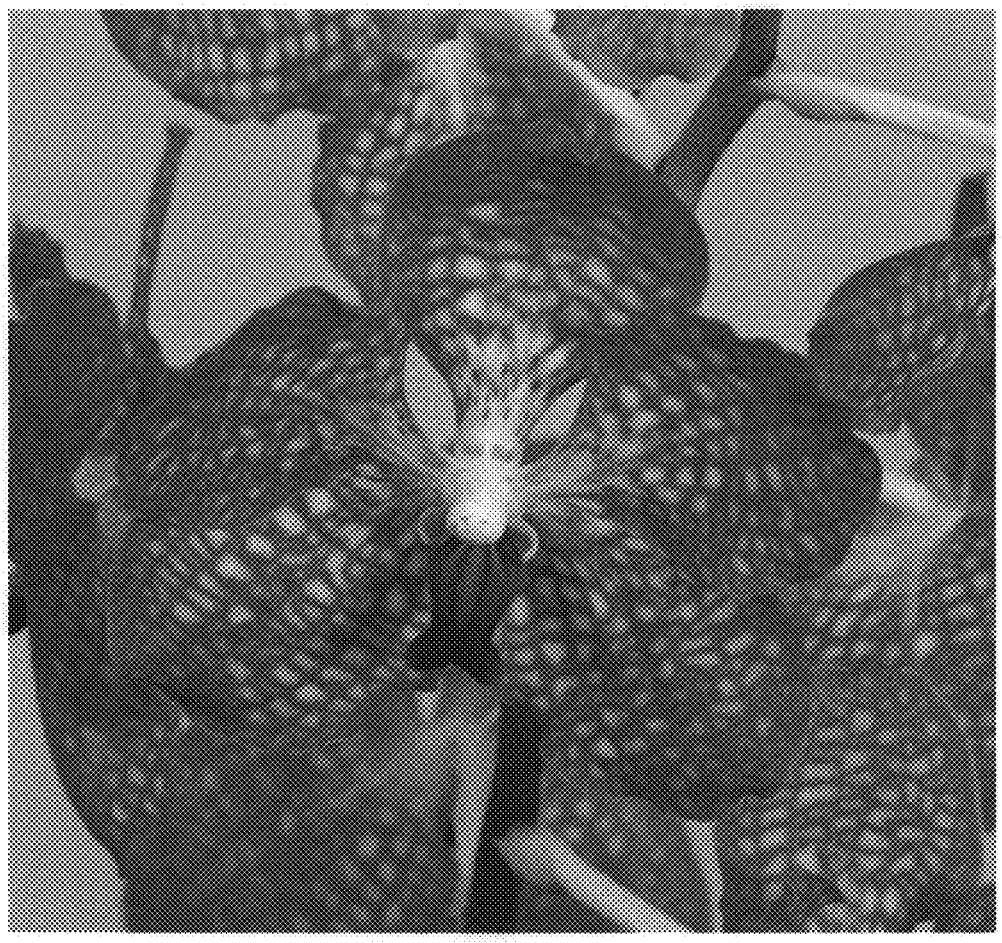
FIG. 3 illustrates, as nearly true as it is reasonably possible to make the same in color photographs of this type, the typical flower of 'SPCDW1521'.

The following observations and measurements made in October of 2016 describe averages from a sample set of six specimens of six year-old 'SPCDW1521' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1521' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1521' and comparisons with other varieties of *Vanda* are provided below.

Plant description:

- *Growth habit.*—Perennial; monopodial, upright. Single monopodial leafy stem, with flowers carried slightly above the leaf plane; inflorescences growing from the leaf axils.
- *Average height from base (plant grown in hanging basket, so no soil line present) to foliar plane.*—39.8 cm.
- *Average height from base (plant grown in hanging basket, so no soil line present) to top of floral plane.*—66.5 cm.
- *Plant spread.*—Average of 40.3 cm.
- *Appropriate container size.*—8 cm by 8 cm rectangular hanging basket.
- *Growth rate.*—Moderate.
- *Plant vigor.*—Moderate.
- *Propagation type.*—Meristematic tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Similar to other *Vanda* varieties.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Moderately dense rooting; with aerial roots only.
- *Dimensions, mature roots.*—67.3 cm long with a diameter of 0.4 cm, on average.
- *Texture.*—Very fleshy; non-fibrous.
- *Color.*—Greyed-green, in between RHS 192B and 192C; root apex is yellow-green, RHS 146A.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—29.8 cm.
- *Diameter.*—0.8 cm.
- *Internode length.*—0.9 cm.
- *Luster.*—Matte.
- *Aspect, main stem.*—Near vertical.
- *Strength.*—Very strong.
- *Color, juvenile.*—Greyed-orange, nearest to RHS 164C.
- *Color, mature.*—Greyed-orange, nearest to RHS 164C.
- *Color at internodes.*—Greyed-orange, nearest to RHS 164C.
- *Pubescence.*—Glabrous.

Foliage:

- *Arrangement.*—Distichous.
- *Dimensions.*—18.5 cm long, excluding the sheath, and 2.7 cm wide.
- *Shape of blade.*—Ligulate; strongly carinate.
- *Aspect.*—Moderately to strongly curved.
- *Apex.*—Unequal praemorse.
- *Base.*—Sheathing.
- *Sheath dimensions.*—3.3 cm long and 1.1 cm wide, on average.
- *Sheath color.*—Yellow-green, a mixture of RHS 145C and 150C.
- *Margin.*—Entire.
- *Pubescence, texture and luster of adaxial surface.*—Glabrous, smooth, and matte.
- *Pubescence, texture and luster of abaxial surface.*—Glabrous, smooth, and matte.
- *Color.*—Juvenile foliage, adaxial surface — Green, nearest to RHS 143C, and suffused with a darker shade of green towards the margins, nearest to RHS 143A. Juvenile foliage, abaxial surface — A mixture of green, nearest to RHS 143B, and yellow-green, nearest to RHS 144A. Mature foliage, adaxial surface — Green, nearest to RHS 143A, and suffused with a darker shade of green towards the margins, nearest to RHS 137B. Mature foliage, abaxial surface — Yellow-green, RHS 144A.
- *Venation.*—Parallel.
- *Venation color, adaxial surface.*—Green, nearest to RHS 143A.
- *Venation color, abaxial surface.*—Yellow-green, RHS N144B.
- *Petiole.*—No petioles present; leaves sessile.

Inflorescence:

*Inflorescence arrangement.*—Axially placed raceme.

*Natural flowering season.*—Autumn into winter.

*Time to flower.*—Approximately 10 months.

*Flowers per inflorescence.*—Average of 14.

*Flowers per plant.*—10 open flowers and 4 flower buds.

*Inflorescence height.*—Approximately 29.4 cm (measured from base of lowest flower to top of upper flower).

*Inflorescence diameter.*—Approximately 22.1 cm.

*Peduncle.*—Dimensions — Approximately 55.0 cm long and 0.7 cm wide. Aspect — Generally at a 35 degree angle to lateral branch axis. Strength — Moderately strong. Texture and luster — Glabrous and moderately glossy. Color — Yellow-green, nearest to RHS 144B.

Bud:

*Length.*—Average of 1.6 cm.

*Diameter.*—Average horizontal diameter is 1.5 cm; the vertical diameter is 2.1 cm.

*Shape.*—Cubic, with a deltoid apex which is pointed downward.

*Pubescence, texture and luster.*—Glabrous, smooth and slightly glossy.

*Color.*—Purple, nearest to RHS 79D, and suffused with yellow green towards the base, nearest to RHS 145D.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum; the two lateral petals slightly overlapping the sepals; sepals do not overlap one another.

*Aspect.*—Flowers are outward-facing to slightly nodding.

*Vertical height.*—Approximately 10.4 cm.

*Diameter.*—Approximately 9.8 cm.

*Depth.*—Approximately 3.2 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 5.3 cm. Width — Approximately 4.5 cm. Shape — Broad ovate to obovate. Apex — Obtuse. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — Violet, in between RHS N88B and N88C, and fading to violet-blue towards the base, nearest to RHS 91D yet lighter; finely dotted with a darker shade of violet, in between RHS N88A and N88B. Color when opening, lower surface — Violet, in between RHS N88C and N88D; blotched with a darker shade of violet, in between RHS N88B and N88C. Color when fully opened, upper surface — A mixture of violet, nearest to RHS N88D, and a lighter shade of violet, in between RHS 85C and 85D. Color when fully opened, lower surface — A mixture of violet, nearest to RHS N88D, and a lighter shade of violet, in between RHS 85C and 85D. Fading, upper surface — Not fading. Fading, lower surface — Not fading. Venation — Densely reticulate. Venation color, fully opened, upper surface — Violet, in between RHS N87A and N88A; closest to RHS N87A. Venation color, fully opened, lower surface — Violet, in between RHS N87A and N88A; closest to RHS N87A.

*Labellum.*—Shape — Three-lobed; the shape of the lateral lobes is broad ovate, and the aspect is involute; the shape of the central lobe is narrow triangular to near oblong, and the aspect is revolute. Length — Central lobe — Approximately 2.2 cm. Lateral lobes — Approximately 0.9 cm. Width — Central lobe — Approximately 1.4 cm. Lateral lobes — Approximately 0.6 cm. Apex — Central lobe — Strongly emarginate. Lateral lobes — Emarginate. Base — Central lobe — Cuneate. Lateral lobes — Cuneate. Margin — Central lobe — Entire; not undulate. Lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — In between violet, nearest to RHS 86A, and violet-blue, nearest to RHS N89A. Lateral lobes — Purple-violet, nearest to RHS N82B, with a yellow-orange basal spot, in between RHS 17B to 17C. Color when opening, lower surface — Central lobe — Violet, nearest to RHS N88A, and fading to a lighter shade of violet towards the base, nearest to RHS 85D. Lateral lobes — Violet, in between RHS 85C to 85D; apex is white, RHS N155A. Color when fully opened, upper surface — Central lobe — Violet-blue, in between RHS 92A and 92B, and fading to violet towards the base, in between RHS 86A and 86B. Lateral lobes — Purple-violet, nearest to RHS N82B, with a yellow-orange basal spot, nearest to RHS 17B. Color when fully opened, lower surface — Central lobe — Violet, nearest to RHS N88A, and fading to a lighter shade of violet towards the base, in between RHS N88B to N88C. Lateral lobes — Violet, nearest to RHS 85B, and fading to a lighter shade of violet towards the base, nearest to RHS 85C. Fading, upper surface — Not fading. Fading, lower surface — Not fading. Venation — Densely reticulate. Venation color, fully opened, upper surface — Central lobe — Violet-blue, in between RHS 92A and 92B, and fading to violet towards the base, in between RHS 86A and 86B. Lateral lobes — Purple-violet, nearest to RHS N82B, with a yellow-orange basal spot, nearest to RHS 17B. Venation color, fully opened, lower surface — Central lobe — Violet, nearest to RHS N88A, and fading to a lighter shade of violet towards the base, in between RHS N88B to N88C. Lateral lobes — Violet, nearest to RHS 85B, and fading to a lighter shade of violet towards the base, nearest to RHS 85C.

*Callosities.*—Dimensions — 1.4 cm long and 0.8 cm wide, on average. Color — Violet, in between RHS N87C and N87D.

*Spurs.*—Quantity — Average of 1. Length — Approximately 1.0 cm. Diameter — Approximately 0.3 cm. Vertical height — Approximately 0.7 cm, at the base.

Shape — Short triangular. Apex — Bluntly acute. Base — Broad cuneate. Pubescence, texture and luster — Glabrous, smooth, and slightly glossy. Color — Violet, RHS 85D.

*Sepals.*—Quantity — Average of 3 unfused sepals. Arrangement — One dorsal sepal and two lateral sepals. Length — Dorsal sepal — Approximately 5.4 cm. Lateral sepals — Approximately 5.8 cm. Width — Dorsal sepal — Approximately 4.2 cm. Lateral sepals — Approximately 5.2 cm. Shape — Dorsal sepal — Broad ovate. Lateral sepals — Broad ovate. Apex — Dorsal sepal — Obtuse. Lateral sepals — Obtuse. Base — Dorsal sepal — Cuneate. Lateral sepals — Cuneate. Margin — Dorsal sepal — Entire; slightly undulated. Lateral sepals — Entire; moderately undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Violet, in between RHS N88B and N88C, and fading to violet-blue towards the base, nearest to RHS 91D yet lighter; finely dotted with a darker shade of violet, in between RHS N88A and N88B. Lateral sepals — Violet, in between RHS N88B and N88C, and fading to violet-blue towards the base, nearest to RHS 91D yet lighter; finely dotted with a darker shade of violet, in between RHS N88A and N88B. Color when opening, lower surface — Dorsal sepal — Violet, in between RHS 85B and 85C; reticulate veining colored violet, in between RHS 86C and 86D. Lateral sepals — Violet, in between RHS 85B and 85C; reticulate veining colored violet, in between RHS 86C and 86D. Color when fully opened, upper surface — Dorsal sepal — A mixture of violet, nearest to RHS N88D, and a lighter shade of violet, in between RHS 85C and 85D. Lateral sepals — A mixture of violet, nearest to RHS N88D, and a lighter shade of violet, in between RHS 85C and 85D. Color when fully opened, lower surface — Dorsal sepal — A mixture of violet, nearest to RHS N88D, and a lighter shade of violet, in between RHS 85C and 85D. Lateral sepals — A mixture of violet, nearest to RHS N88D, and a lighter shade of violet, in between RHS 85C and 85D. Fading, upper surface — Not fading. Fading, lower surface — Not fading. Venation — Densely reticulate. Venation color, fully opened, upper surface — Dorsal sepal — Violet, in between RHS N87A and N88A; closest to RHS N87A. Lateral sepals — Violet, in between RHS N87A and N88A; closest to RHS N87A. Venation color, fully opened, lower surface — Dorsal sepal — Violet, in between RHS N87A and N88A; closest to RHS N87A. Lateral sepals — Violet, in between RHS N87A and N88A; closest to RHS N87A.

*Pedicels.*—Length — Approximately 6.2 cm. Diameter — Approximately 0.45 cm. Angle — Approximately 85 degree angle to peduncle axis. Strength — Moderate. Texture — Glabrous, axially angled with 5 "ribs", axially twisted (due to resupination). Luster — Glossy. Color — White, RHS NN155D.

*Bract.*—Quantity — One bract present at the base of each pedicel. Shape — Broad ovate; folded around the base of each pedicel. Dimensions — Average of 1.6 cm long and 1.4 cm wide. Apex — Broad acute. Base — Broad cuneate. Margins — Entire. Color, both surfaces — Yellow-green, nearest to RHS 151C, and suffused with greyed-purple at the apex, RHS N186D.

Reproductive organs:

*Column.*—Length — Approximately 0.7 cm. Diameter — Approximately 0.7 cm. Color — White, nearest to RHS NN155C, and fading to violet towards the base, nearest to RHS 84C.

*Ovary.*—Position — Inferior. Diameter — Approximately 0.2 cm. Color — Yellow-green, RHS 150C.

*Pollinia color.*—Yellow-orange, nearest to RHS 14A.

Seed and fruit: No fruit and seed production has been detected to date.

COMPARISON WITH THE PARENT PLANTS

Plants of the new cultivar 'SPCDW1521' differ from the unnamed *Vanda* seed parent, 'M217' (not patented), by the characteristics described in Table 1.

TABLE 1

| Characteristic | 'SPCDW1521' | 'M217' |
|---|---|---|
| General coloration of the petals and sepals (excluding venation) when fully opened. | Violet. | Purple. |
| Plant spread. | Narrower than 'M217'. | Wider than 'SPCDW1521'. |
| Flower size. | Larger than 'M217'. | Smaller than 'SPCDW1521'. |
| Plant vigor. | More vigorous; easier to cultivate and quicker to flower when compared to 'M217'. | Less vigorous; more difficult to cultivate and slower to flower when compared to 'SPCDW1521'. |

Plants of the new cultivar 'SPCDW1521' differ from the unnamed *Vanda* pollen parent, 'CS76' (not patented), by the characteristics described in Table 2.

TABLE 2

| Characteristic | 'SPCDW1521' | 'CS76' |
|---|---|---|
| Length of foliage. | Longer than 'CS76'. | Shorter than 'SPCDW1521'. |
| Inflorescence dimensions. | Flowers are more loosely held on the inflorescence; inflorescence is therefore less compact. | Flowers are more tightly held on the inflorescence; inflorescence is therefore more compact. |
| Thickness of petals and sepals. | Petals and sepals are thicker than those of 'C576'. | Petals and sepals are less thick than those of 'SPCDW1521'. |

COMPARISON WITH THE MOST SIMILAR *VANDA* CULTIVAR KNOWN TO THE INVENTOR

Plants of the new cultivar 'SPCDW1521' are most similar to the cultivar, *Vanda* 'Blue Magic' (not patented in the United States). A comparison of 'SPCDW1521' with *Vanda* 'Blue Magic' is described in Table 3.

TABLE 3

| Characteristic | 'SPCDW1521' | 'Blue Magic' |
|---|---|---|
| Length of foliage. | Longer than 'Blue Magic'. | Shorter than 'SPCDW1521'. |
| Foliage attitude. | Semi-erect. | More horizontal. |
| General coloration of the foliage. | Darker green than 'Blue Magic'. | Lighter green than 'SPCDW1521'. |
| Root density. | Producing more roots than 'Blue Magic'. | Producing fewer roots than 'SPCDW1521'. |
| Number of flowers per inflorescence. | More flowers per inflorescence. | Fewer flowers per inflorescence. |
| Diameter of the peduncle. | Larger diameter. | Smaller diameter. |
| Flower size. | Smaller than 'Blue Magic'. | Larger than 'SPCDW1521'. |
| Petal and sepal aspect. | Petals and sepals are less spiraled in a propeller-like fashion than those of 'Blue Magic'. | Petals and sepals are more spiraled in a propeller-like fashion than those of 'SPCDW1521'. |
| General coloration of the petals and sepals (excluding venation) when fully opened. | Violet. | Violet, yet closer in color to violet-blue. |
| General coloration of the petal and sepal venation when fully opened. | Darker shade of violet-blue. | Lighter shade of violet-blue. |

TABLE 3-continued

| Characteristic | 'SPCDW1521' | 'Blue Magic' |
|---|---|---|
| Prominence of the color pattern (venation) on the petals and sepals when fully opened. | More prominent tessellation, especially towards the apex of sepals. | Less prominent tessellation, especially towards the apex of sepals. |
| Width of the labellum. | Wider than 'Blue Magic'. | More narrow than 'SPCDW1521'. |
| Central lobe of the labellum; general coloration when fully open. | Darker shade of violet. | Lighter shade of violet. |
| Width of the central lobe of the labellum, at the apex. | Wider than 'Blue Magic'. | More narrow than 'SPCDW1521'. |
| Lateral lobes of the labellum; general coloration when fully open. | Darker shade of violet. | Lighter shade of violet. |
| Aspect of the lateral lobes of the labellum. | Moderately involute. | Strongly involute. |
| Color of callosities. | Lighter shade of violet. | Darker shade of violet. |

That which is claimed is:

1. A new and distinct variety of *Vanda* plant named 'SPCDW1521', substantially as described and illustrated herein.

* * * * *